United States Patent [19]

Terada et al.

[11] Patent Number: 5,175,345

[45] Date of Patent: Dec. 29, 1992

[54] PROCESS FOR PRODUCING 2-FLUOROISOBUTYRIC ACID ESTER

[75] Inventors: Izumi Terada; Masahiro Nishii; Kazufumi Nakamura, all of Sodegaura, Japan

[73] Assignee: Idemitsu Kosan Company Limited, Tokyo, Japan

[21] Appl. No.: 854,734

[22] Filed: Mar. 23, 1992

[30] Foreign Application Priority Data

Mar. 27, 1991 [JP] Japan .................................. 3-63114
Sep. 4, 1991 [JP] Japan .................................. 3-224433

[51] Int. Cl.$^5$ ...................... C07C 53/15; C07C 53/21; C07C 69/63; C07B 39/00
[52] U.S. Cl. .................................. 560/227; 560/226; 562/602; 562/603; 562/605
[58] Field of Search ............... 560/226, 227; 562/602, 562/603, 605

[56] References Cited

U.S. PATENT DOCUMENTS 5,049,676  9/1991  Metivier et al. .................... 560/226

FOREIGN PATENT DOCUMENTS 2039546  2/1987  Japan .................................. 560/227
63-264465  1/1988  Japan .
63-51379  3/1988  Japan .
WO88/02368  4/1988  Japan .
63-238071  4/1988  Japan .
WO90/09378  8/1990  Japan .

OTHER PUBLICATIONS

Genssler et al., "Fluorination of Methyl Isobutyrate with Perchoryl Fluoride", J. Org. Chem. NOTES, vol. 33, No. 11, Nov. 1968, 4279-4281.
Purrington et al., "Preparation of α-Fluoro Carboxylic Acids and Derivatives", J. Org. Chem., vol. 55, 1990, 3423-3424.

Primary Examiner—Jose G. Dees
Assistant Examiner—Keith MacMillan
Attorney, Agent, or Firm—Frishauf, Holtz, Goodman & Woodward

[57] ABSTRACT

A 2-fluoroisobutyric acid ester can be obtained at a high yield in one pot by reacting a 2-hydroxyisobutyric acid ester with fluorosulfuric acid in the absence or presence of a hydrogen fluoride source, or by reacting a 2-hydroxyisobutyric acid ester with chlorosulfuric acid in the presence of a hydrogen fluoride source.

30 Claims, No Drawings

PROCESS FOR PRODUCING 2-FLUOROISOBUTYRIC ACID ESTER

BACKGROUND OF THE INVENTION

1. Field of the Invention

The present invention relates to a process for producing a 2-fluoroisobutyric acid ester. The 2-fluoroisobutyric acid esters obtained by the present process are useful as intermediates of triazine type herbicides.

2. Description of the Prior Arts

WO 90/09378 discloses triazine type herbicides which are triazine derivatives each having a triazine ring substituted with a phenoxyalkylamine group, such as shown by the following formula.

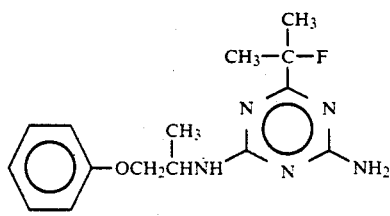

According to the document, these triazine type herbicides have remarkable advantages in that they not only show an excellent herbicidal effect but also give no phytotoxicity to paddy rice.

These phenoxyalkylamine group-substituted triazine type herbicides can be obtained by, for example, reacting a 2-fluoroisobutyric acid ester with 2-phenoxy-1-methyl-ethylbiguanide. As the process for production of a 2-fluoroisobutyric acid ester, used in the above reaction, J. Org. Chem. 33 4279 (1968) discloses a process which comprises subjecting a 2-bromoisobutyric acid ester and AgF to a halogen exchange reaction to obtain a 2-fluoroisobutyric acid ester. The reaction is shown by the following reaction formula.

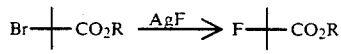

As other process for producing the 2-fluoroisobutyric acid ester, J. Org. Chem. 55 3423 (1990) discloses a process which comprises reacting methyl isobutyrate with trimethylsilyl chloride in the presence of lithium diisopropylamine (LDA) to obtain 1-methoxyl-1-(trimethylsilyloxy)-2-methylpropene and then reacting it with $F_2$ in $CFCl_3$ to obtain a 2-fluoroisobutyric acid ester. The reaction is shown by the following reaction formula.

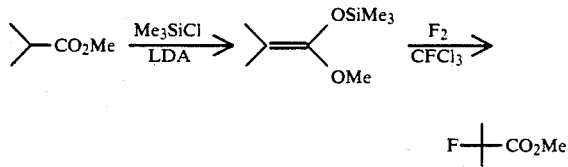

The above conventional process for producing a 2-fluoroisobutyric acid ester from a 2-bromoisobutyric acid ester, however, has had a drawback in that a methacrylic acid ester is generated as a by-product in the process, making low the yield of desired product, i.e. 2-fluoroisobutyric acid ester. The process further has had a drawback in that the AgF used as a reactant in the halogen exchange reaction is expensive, making high the production cost.

The other conventional process for producing a 2-fluoroisobutyric acid ester from methyl isobutyrate, has had a drawback in that the yield of desired product is low because the reaction is conducted in two steps. The process further has had a drawback in that each of the first and second steps must be conducted at an extremely low temperature ($-78°$ C.), requiring a special facility such as refrigerator and the like.

SUMMARY OF THE INVENTION

Hence, the object of the present invention is to provide a process which can produce a 2-fluoroisobutyric acid ester at a high yield and inexpensively using a simple facility.

The present inventors found that a 2-fluoroisobutyric acid ester can be produced at a high yield and inexpensively using a simple facility by (1) reacting a 2-hydroxyisobutyric acid ester with fluorosulfuric acid in the absence or presence of a hydrogen fluoride source, or (2) reacting a 2-hydroxyisobutyric acid ester with chlorosulfuric acid in the presence of a hydrogen fluoride source. The present invention has been completed based on the above finding.

The gist of the present invention lies in a process for producing a 2-fluoroisobutyric acid ester, which comprises reacting a 2-hydroxyisobutyric acid ester with fluorosulfuric acid in the absence or presence of a hydrogen fluoride source.

The gist of the present invention also lies in a process for producing a 2-fluoroisobutyric acid ester, which comprises reacting a 2-hydroxyisobutyric acid ester with chlorosulfuric acid in the presence of a hydrogen fluoride source.

DETAILED DESCRIPTION OF THE INVENTION

The present invention is hereinafter described in detail.

In the present process for producing a 2-fluoroisobutyric acid ester, the 2-hydroxyisobuytric acid ester used as a starting material includes, for example, a 2-hydroxyisobutyric acid ester represented by the following general formula (I).

(I)

wherein R is a lower alkyl group. In the general formula (I) representing the 2-hydroxyisobutyric acid ester, R (lower alkyl group) includes methyl group, ethyl group, n-propyl group, i-propyl group, n-butyl group, i-butyl group, sec-butyl group and tert-butyl group.

According to the present invention, a 2-fluoroisobutyric acid ester represented by the following general formula (II)

(II)

(R is a lower alkyl group) can be obtained by (1) reacting the above 2-hydroxyisobutyric acid ester with fluorosulfuric acid in the absence or presence of a hydrogen fluoride source, or (2) reacting the above 2-hydroxyisobutyric acid ester with chlorosulfuric acid in the presence of a hydrogen fluoride source.

When fluorosulfuric acid is used as a reactant to be reacted with the 2-hydroxyisobutyric acid ester, a 2-fluoroisobutyric acid ester can be obtained even in the absence of a hydrogen fluoride source; however, the presence of a hydrogen fluoride source can yield an advantage of increased yield. Meanwhile, when chlorosulfuric acid is used, the presence of a hydrogen fluoride source is requisite. The hydrogen fluoride source includes, for example, anhydrous hydrogen fluoride and hydrogen fluoride containing an amine in an amount of 0-50% by weight, preferably 0-5% by weight. The amine includes, for example, aromatic amines such as pyridine, melamine, collidine and the like, and tertiary aliphatic amines such as trimethylamine, triethylamine, tributylamine and the like. The hydrogen fluoride source can be any as long as it is in the form of hydrogen fluoride at the time of the reaction. Hence, it is possible to feed a hydrogen fluoride precursor into the reaction system and generate hydrogen fluoride in the reaction system.

The reaction temperature is not critical but is preferably 0°-70° C., particularly preferably 10°-50° C. The reaction pressure is not critical, either, and the reaction can be conducted under atmospheric pressure or applied pressure.

The process of the present invention makes it possible to produce a 2-fluoroisobutyric acid ester from a 2-hydroxyisobutyric acid ester at a high yield and inexpensively using a simple facility. Therefore, the process has a very high industrial value.

The 2-hydroxyisobutyric acid ester used as a starting material in the present process can be produced by a process described in U.S. Pat. No. 3,536,750, which comprises reacting methyl isobutyrate with 5% $H_3BO_3$, or by a process described in Austrian Patent No. 360,499, which comprises treating 2-hydroxyisobutyramide (which is presumed to be produced by the hydration of acetone cyanhydrin) with a $H_2SO_4$-MeOH mixture.

In the former process (U.S. Pat. No. 3,536,750), however, the conversion is extremely low (20%) and the selectivity is not sufficiently high (75%) and gives a low yield of 15%. Further, a high reaction temperature of 140°-175° C. is required.

In the latter process (Austrian Patent No. 360,499), a high reaction temperature of, for example, 120° C. is required in the latter step for obtaining an ester from an amide, and a relatively long reaction time of, for example, 5 hours is required. Further, the 2-hydroxyisobutyramide obtained from acetone cyanhydrin in the former step need be separated and purified, and the process makes it impossible to produce a 2-hydroxyisobutyric acid ester directly from acetone cyanhydrin in one pot (a single reactor).

Hence, the present inventors made study in order to find a process which can produce a 2-hydroxyisobutyric acid ester from acetone cyanhydrin at a high yield in one pot. As a result, the present inventors found that a 2-hydroxyisobutyric acid ester can be produced at a high yield in one pot by reacting acetone cyanhydrin with a lower alcohol and a hydrogen halide and then hydrolyzing the reaction product.

The above process for producing a 2-hydroxyisobutyric acid ester is described in detail below.

The acetone cyanhydrin used as a starting material is a compound represented by the following formula (III), obtained by reacting acetone with hydrogen cyanide.

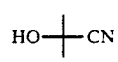  (III)

This acetone cyanhydrin is reacted with an alcohol represented by the following general formula (IV)

ROH  (IV)

(R is a lower alkyl group) and a hydrogen halide represented by the following general formula (V)

HX  (V)

wherein X is a halogen atom, to obtain an intermediate represented by the following general formula (VI)

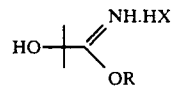  (VI)

wherein R is a lower alkyl group and X is a halogen atom.

The alcohol (ROH) used in the above reaction includes lower alcohols such as methanol, ethanol, n-propanol, i-propanol, n-butanol, i-butanol, sec-butanol, tert-butanol and the like. The amount of the alcohol used is preferably 1-10 times, particularly preferably 1.5-5 times in equivalents as much as that of acetone cyanhydrin. The hydrogen halide (HX) includes hydrogen chloride, hydrogen bromide, etc. The amount of the hydrogen halide used is preferably 0.5-3.0 times, particularly preferably 1.0-2.0 times in equivalents as much as that of acetone cyanhydrin. Preferably, the hydrogen halide is blown in a gaseous state. The reaction temperature is not particularly restricted, but is preferably −10° C. to 70° C., particularly preferably 0°-40° C. The reaction time has no particular restriction, either, but is preferably 1-3 hours.

The above-obtained intermediate represented by the general formula (V) is hydrolyzed without being subjected to separation and purification, to obtain a 2-hydroxyisobutyric acid ester represented by the following general formula (I)

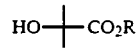  (I)

wherein R is a lower alkyl group. The amount of water used in the hydrolysis is preferably 1-5 times, particularly preferably 1-3 times the weight of acetone cyanhydrin. In this hydrolysis reaction, it is not requisite to newly add an acid because a hydrogen halide is added in the preceding reaction, but an acid can be added as necessary. The reaction temperature is not particularly restricted, but is preferably 10°-80° C., particularly preferably 20°-50° C. The reaction time is not particularly restricted, either, but is preferably 0.5-30 hours, particularly preferably 1-20 hours.

The above process for producing a 2-hydroxyisobutyric acid ester makes it possible to produce a 2-hydroxyisobutyric acid ester at a high yield in one pot (a single reactor) by reacting acetone cyanhydrin with a lower alcohol and a hydrogen halide to obtain an intermediate and successively hydrolyzing the intermediate without subjecting the intermediate to separation and purification. Therefore, the process has a very high industrial value.

The present invention is hereinafter described in more detail by way of Examples. However, the present invention is by no means restricted to these Examples.

EXAMPLE 1

Production of 2-fluoroisobutyric acid ester 8.2 g (82.0 mM) of fluorosulfuric acid was placed in a teflon-made reactor and cooled to 0° C. Thereto was added 4.8 g (40.7 mM) of methyl 2-hydroxyisobutyrate in 30 minutes, with stirring. The resulting mixture was stirred at 0° C. for 1 hour. Then, the mixture was returned to room temperature (20° C.) and stirred for 60 hours to give rise to a reaction. After the completion of the reaction, the reaction mixture was poured into ice water. The resulting mixture was extracted with methylene chloride. The extract was dried over anhydrous sodium sulfate and subjected to vacuum distillation to remove methylene chloride. The resulting residue was subjected to distillation at 150 mmHg to obtain 0.93 g (yield: 19%) of methyl 2-fluoroisobutyrate having a boiling point of 106°-107° C.

EXAMPLE 2

Production of 2-fluoroisobutyric acid ester

Into a 50-ml autoclave having a teflon-made internal cylinder were placed 9 ml of a hydrogen fluoride/pyridine mixture [hydrogen fluoride/pyridne = 70/30 (wt/wt), containing about 300 mM of hydrogen fluoride] and 9.15 g (91.5 mM) of fluorosulfuric acid. The autoclave contents were cooled to 0° C. Thereto was added 3.6 g (30.5 mM) of methyl 2-hydroxyisobutyrate. The resulting mixture was subjected to a reaction at 40° C. for 4 hours. After the completion of the reaction, the reaction mixture was poured into ice water. The resulting mixture was extracted with methylene chloride. The extract was dried over anhydrous sodium sulfate and subjected to vacuum distillation to remove methylene chloride. The resulting residue was subjected to distillation at 70° C. (150 mmHg) to obtain 1.9 g (yield: 52%) of methyl 2-fluoroisobutyrate having a boiling point of 106°-107° C.

EXAMPLES 3-11

Production of 2-fluoroisobutyric acid esters

2-Fluoroisobutyric acid esters of Examples 3-6 were obtained in the same manner as in Example 2 except that the amount of fluorosulfuric acid, the hydrogen fluoride source, the amount of hydrogen fluoride source, the reaction temperature and the reaction time were changed.

2-Fluoroisobutyric acid esters of Examples 7-9 were obtained in the same manner as in Example 2 except that 4.8 g (40.7 mM) of methyl 2-hydroxyisobutyrate was used, and the amount of fluorosulfuric acid, the hydrogen fluoride source, the amount of hydrogen fluoride source, the reaction temperature and the reaction time were changed.

Methyl 2-fluoroisobutyrate of Example 10 was obtained in the same manner as in Example 2 except that chlorosulfuric acid was used in place of fluorosulfuric acid.

Methyl 2-fluoroisobutyrate of Example 11 was obtained in the same manner as in Example 10 except that the reaction temperature was changed to room temperature and the reaction time was changed.

The reaction conditions and results of Examples 3-11 are shown in Table 1, together with those of Examples 1-2.

EXAMPLE 12

Production of 2-fluoroisobutyric acid ester

Into a 50-ml autoclave having a teflon-made internal cylinder were placed 9 ml of a hydrogen fluoride/pyridine mixture [hydrogen fluoride/pyridne = 70/30 (wt/wt), containing about 300 mM of hydrogen fluoride] and 9.15 g (91.5 mM) of fluorosulfuric acid. The autoclave contents were cooled to 0° C. Thereto was added 4.0 g (30.5 mM) of ethyl 2-hydroxyisobutyrate. The resulting mixture was subjected to a reaction at 40° C. for 4 hours. After the completion of the reaction, the reaction mixture was poured into ice water. The resulting mixture was extracted with methylene chloride. The extract was dried over anhydrous sodium sulfate and subjected to vacuum distillation to remove methylene chloride. The resulting residue was subjected to distillation to obtain 2.1 g (yield: 52%) of ethyl 2-fluoroisobutyrate having a boiling point of 124°-126° C.

EXAMPLE 13

Ethyl 2-fluoroisobutyrate was obtained in the same manner as in Example 12 except that the reaction temperature and time were changed. The reaction conditions and results are shown in Table 1.

EXAMPLE 14

Ethyl 2-fluoroisobutyrate was obtained in the same manner as in Example 12 except that fluorosulfuric acid was substituted by chlorosulfuric acid. The reaction conditions and results are shown in Table 1.

TABLE 1

| Example | Reaction conditions | | | | | Reaction results |
|---|---|---|---|---|---|---|
| | XSO$_3$H | | Hydrogen fluoride source | | Temp. (°C.) | Time (hr) | Yield (%) |
| 1 | FSO$_3$H | 8.2 g (82.0 mM)* | — | — | 20 | 60 | 19 |
| 2 | " | 9.15 g (91.5 mM)** | HF/Py*** 70/30 (wt/wt) | 9 ml | 40 | 4 | 52 |
| 3 | " | 10.5 g (105 mM)** | HF/Py*** 70/30 (wt/wt) | 21 ml | 50 | 7 | 32 |
| 4 | " | 7.3 g (73 mM)** | HF/Py*** 70/30 (wt/wt) | 6 ml | 40 | 7 | 41 |
| 5 | " | 9.15 g (91.5 mM)** | HF/Py*** 70/30 (wt/wt) | 9 ml | 40 | 7 | 45 |
| 6 | " | " | HF/Py*** 70/30 (wt/wt) | 9 ml | 20 | 20 | 49 |

TABLE 1-continued

| Example | XSO₃H | | Reaction conditions | | Temp. (°C.) | Time (hr) | Reaction results Yield (%) |
|---|---|---|---|---|---|---|---|
| | | | Hydrogen fluoride source | | | | |
| 7 | " | 19.3 g (193 mM)** | HF/Py*** 95/5 (wt/wt) | 13.2 g | 20 | 18 | 73 |
| 8 | " | 7.1 g (71 mM)** | AHF**** | 4.1 g | 20 | 18 | 61 |
| 9 | " | 19.3 g (193 mM)** | HF/Py*** 70/30 (wt/wt) | 12.5 g | 20 | 18 | 75 |
| 10 | ClSO₃H | 10.1 g (91.5 mM)** | HF/Py*** 70/30 (wt/wt) | 9 ml | 40 | 4 | 47 |
| 11 | " | " | HF/Py*** 70/30 (wt/wt) | 9 ml | 20 | 24 | 51 |
| 12 | FSO₃H | 9.15 g (91.5 mM)** | HF/Py*** 70/30 (wt/wt) | 9 ml | 40 | 4 | 52 |
| 13 | " | " | HF/Py*** 70/30 (wt/wt) | 9 ml | 20 | 24 | 51 |
| 14 | ClSO₃H | 10.1 g (91.5 mM)** | HF/Py*** 70/30 (wt/wt) | 9 ml | 40 | 4 | 50 |

*Amount fed to 4.8 g (40.7 mM) of methyl 2-hydroxyisobutyrate
**Amount fed to 3.6 g (30.5 mM) of methyl 2-hydroxyisobutyrate
***Hydrogen fluoride-pyridine mixture
****Anhydrous hydrogen fluoride As is clear from Table 1, when fluorosulfuric acid was used as a reactant, a reaction proceeded at room temperature even if no hydrogen fluoride source was present, whereby methyl 2-fluoroisobutyrate could be obtained (Example 1). When a hydrogen fluoride source (HF/Py) was used together with fluorosulfuric acid, 2-fluoroisobutyric acid ester could be obtained at a high yield in a short time (Examples 2-9, 12-14). When a reaction was conducted using chlorosulfuric acid in place of fluorosulfuric acid, in the presence of a hydrogen fluoride source (HF/Py), 2-fluoroisobutyric acid ester could be obtained at a high yield (Examples 10-11).

As illustrated in the above Examples 1-14, the present invention provides a process which can produce a 2-fluoroisobutyric acid ester at a high yield and inexpensively using a simple facility.

EXAMPLE 15

Production of 2-hydroxyisobutyric acid ester 20 g (0.235 M) of acetone cyanhydrin was dissolved in 15 g (0.47 M) of methanol, and the solution was cooled to 0° C. Thereinto was blown 12 g (0.33 M) of hydrogen chloride gas while care was taken so that the temperature of the solution did not exceed 10° C., after which stirring was conducted at 5° C. for 1.5 hours to obtain an intermediate represented by the following formula.

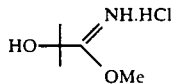

Without separating the intermediate for purification, the reaction mixture containing the intermediate was mixed with 40 ml of water. The resulting mixture was stirred at room temperature for 1 hour. The reaction mixture was neutralized with sodium hydrogencarbonate, followed by extraction with methylene chloride. The extract was dried over anhydrous sodium sulfate and subjected to distillation to obtain 22.8 g of methyl 2-hydroxyisobutyrate. The yield was as high as 82.4%.

EXAMPLES 16-19

Production of 2-hydroxyisobutyric acid esters

Methyl 2-hydroxyisobutyrate was obtained at yields as high as 70-82% in the same manner as in Example 15 except that the reaction conditions were changed as shown in Table 2.

TABLE 2

| Example | Alcohol-hydrogen halide addition reaction | | | | | Hydrolysis reaction | | | Yield (%) |
|---|---|---|---|---|---|---|---|---|---|
| | ACH* | MeOH | HCl | Temp. | Time (hr) | Water (ml) | Temp. | Time (hr) | |
| 15 | 20 g (0.295 M) | 15 g (0.47 M) | 12 g (0.33 M) | 5° C. | 1.5 | 40 | Room temp. | 1 | 82.4 |
| 16 | 20 g (0.295 M) | 20 g (0.63 M) | 23 g (0.63 M) | Room temp. | 1 | 40 | Room temp. | 2 | 71 |
| 17 | 20 g (0.295 M) | 20 g (0.63 M) | 15.6 g (0.43 M) | 0° C. Room temp. | 1 1 | 40 | Room temp. | 1.5 | 75 |
| 18 | 20 g (0.295 M) | 11.3 g (0.35 M) | 12.3 g (0.34 M) | 30° C. | 1 | 20 | Room temp. | 7 | 82 |
| 19 | 20 g (0.295 M) | 11.3 g (0.35 M) | 13.0 g (0.36 M) | 30° C. | 1 | 40 | Room temp. | 2 | 70 |

*ACH: Acetone cyanhydrin

As illustrated in Examples 15-19, a 2-hydroxyisobutyric acid ester can be produced from acetone cyanhydrin in one pot at a high yield. The 2-hydroxyisobutyric acid ester can be preferably used as a starting material for 2-fluoroisobutyric acid ester.

What is claimed is:

1. A process for producing a 2-fluoroisobutyric acid ester, which comprises reacting a 2-hydroxyisobutyric acid ester with fluorosulfuric acid in the absence or presence of a hydrogen fluoride source.

2. A process according to claim 1, wherein the 2-hydroxyisobutyric acid ester is a compound represented by the following general formula (I)

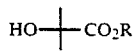  (I)

wherein R is a lower alkyl group.

3. A process according to claim 2, wherein the R in the general formula (I) is at least one member selected from the group consisting of methyl group, ethyl group, n-propyl group, i-propyl group, n-butyl group, i-butyl group, sec-butyl group and tert-butyl group.

4. A process according to claim 1, wherein the hydrogen fluoride source is anhydrous hydrogen fluoride, or hydrogen fluoride containing an amine in an amount of 1-50% by weight.

5. A process according to claim 4, wherein the amine is an aromatic amine or a tertiary aliphatic amine.

6. A process according to claim 1, wherein a hydrogen fluoride precursor is fed into the reaction system and hydrogen fluoride is generated in the reaction system.

7. A process according to claim 1, wherein the reaction is conducted at 0°-70° C.

8. A process according to claim 1, wherein the 2-hydroxyisobutyric acid ester is obtained by reacting acetone cyanhydrin with a lower alcohol and a hydrogen halide and then hydrolyzing the reaction product.

9. A process according to claim 8, wherein the lower alcohol is one member selected from the group consisting of methanol, ethanol, n-propanol, i-propanol, n-butanol, i-butanol, sec-butanol and tert-butanol.

10. A process according to claim 8, wherein the amount of the lower alcohol is 1-10 times in equivalents as much as that of acetone cyanhydrin.

11. A process according to claim 8, wherein the hydrogen halide is hydrogen chloride or hydrogen bromide.

12. A process according to claim 8, wherein the amount of the hydrogen halide is 0.5-3.0 times in equivalents as much as that of acetone cyanhydrin.

13. A process according to claim 8, wherein the reaction of acetone cyanhydrin with a lower alcohol and a hydrogen halide is conducted at temperatures of −10° C. to 70° C.

14. A process according to claim 8, wherein the amount of water in hydrolysis is 1-5 times the weight of acetone cyanhydrin.

15. A process according to claim 8, wherein the hydrolysis reaction is conducted at temperatures of 10°-80° C.

16. A process for producing a 2-fluoroisobutyric acid ester, which comprises reacting a 2-hydroxyisobutyric acid ester with chlorosulfuric acid in the presence of a hydrogen fluoride source.

17. A process according to claim 16, wherein the 2-hydroxyisobutyric acid ester is a compound represented by the following general formula (I)

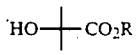  (I)

wherein R is a lower alkyl group.

18. A process according to claim 17, wherein the R in the general formula (I) is at least one member selected from the group consisting of methyl group, ethyl group, n-propyl group, i-propyl group, n-butyl group, i-butyl group, sec-butyl group and tert-butyl group.

19. A process according to claim 16, wherein the hydrogen fluoride source is anhydrous hydrogen fluoride, or hydrogen fluoride containing an amine in an amount of 1-50% by weight.

20. A process according to claim 19, wherein the amine is an aromatic amine or a tertiary aliphatic amine.

21. A process according to claim 16, wherein a hydrogen fluoride precursor is fed into the reaction system and hydrogen fluoride is generated in the reaction system.

22. A process according to claim 16, wherein the reaction is conducted at 0°-70° C.

23. A process according to claim 16, wherein the 2-hydroxyisobutyric acid ester is obtained by reacting acetone cyanhydrin with a lower alcohol and a hydrogen halide and then hydrolyzing the reaction product.

24. A process according to claim 23, wherein the lower alcohol is one member selected from the group consisting of methanol, ethanol, n-propanol, i-propanol, n-butanol, i-butanol, sec-butanol and tert-butanol.

25. A process according to claim 23, wherein the amount of the lower alcohol is 1-10 times in equivalents as much as that of acetone cyanhydrin.

26. A process according to claim 23, wherein the hydrogen halide is hydrogen chloride or hydrogen bromide.

27. A process according to claim 23, wherein the amount of the hydrogen halide is 0.5-3.0 times in equivalents as much as that of acetone cyanhydrin.

28. A process according to claim 23, wherein the reaction of acetone cyanhydrin with a lower alcohol and a hydrogen halide is conducted at temperatures of −10° C. to 70° C.

29. A process according to claim 23, wherein the amount of water in hydrolysis is 1-5 times the weight of acetone cyanhydrin.

30. A process according to claim 23, wherein the hydrolysis reaction is conducted at temperatures of 10°-80° C.

* * * * *

UNITED STATES PATENT AND TRADEMARK OFFICE
CERTIFICATE OF CORRECTION

PATENT NO.   : 5,175,345
DATED        : December 29, 1992
INVENTOR(S)  : TERADA et al It is certified that error appears in the above-identified patent and that said Letters Patent is hereby corrected as shown below:

TITLE PAGE -

In Section [30] Foreign Application Priority Data, delete the following:

"Sep. 4, 1991 [JP]  Japan.........3-224433"

Signed and Sealed this

Fourth Day of January, 1994

Attest:

*Attesting Officer*

BRUCE LEHMAN
*Commissioner of Patents and Trademarks*